(12) United States Patent
Nishizaki et al.

(10) Patent No.: US 9,936,874 B2
(45) Date of Patent: *Apr. 10, 2018

(54) OPTICAL MEASUREMENT APPARATUS AND LIGHT IRRADIATION/RECEPTION METHOD

(71) Applicant: FUJI XEROX CO., LTD., Minato-ku, Tokyo (JP)

(72) Inventors: Saori Nishizaki, Ebina (JP); Taku Kinoshita, Ebina (JP); Kazutaka Takeda, Ebina (JP); Hideaki Ozawa, Ebina (JP); Kazuyuki Matsushita, Ebina (JP); Kohei Yukawa, Ebina (JP); Sho Kimura, Ebina (JP); Hideo Nakayama, Ebina (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/475,365

(22) Filed: Mar. 31, 2017

(65) Prior Publication Data

US 2017/0202458 A1 Jul. 20, 2017

Related U.S. Application Data

(63) Continuation of application No. PCT/JP2015/083110, filed on Nov. 25, 2015.

(30) Foreign Application Priority Data

Nov. 26, 2014 (JP) .................................. 2014-239091
Nov. 26, 2014 (JP) .................................. 2014-239092

(Continued)

(51) Int. Cl.
*G03B 29/00* (2006.01)
*A61B 3/16* (2006.01)
(Continued)

(52) U.S. Cl.
CPC ............ *A61B 3/165* (2013.01); *A61B 5/1455* (2013.01); *A61B 5/14532* (2013.01)

(58) Field of Classification Search
USPC .......................................................... 396/18
See application file for complete search history.

(56) References Cited

U.S. PATENT DOCUMENTS 2,430,851 A * 11/1947 Allen ..................... A61B 3/117
351/205
4,398,812 A * 8/1983 Kelman ............... A61B 3/1005
351/205

(Continued)

FOREIGN PATENT DOCUMENTS

JP 9-138231 A 5/1997
JP 2002-570 A 1/2002

(Continued)

OTHER PUBLICATIONS

International Search Report dated Feb. 16, 2016 issued by the International Searching Authority in counterpart International Application No. PCT/JP2015/083110 (PCT/ISA/210).

(Continued)

*Primary Examiner* — Rodney Fuller
(74) *Attorney, Agent, or Firm* — Sughrue Mion, PLLC

(57) ABSTRACT

An optical measurement apparatus includes: an emission section that emits light such that the light travels across an anterior chamber of an eyeball of a measurement subject; a light reception section that receives light that is emitted from the emission section and travels across the anterior chamber; and a positioning section that performs positioning of one of the emission section and the light reception section at a position where skin on a periphery of an inner canthus of the eyeball is squeezed into an eye socket accommodating the eyeball.

13 Claims, 9 Drawing Sheets

(30) Foreign Application Priority Data

| Nov. 26, 2014 | (JP) | ................................. | 2014-239093 |
| Aug. 18, 2015 | (JP) | ................................. | 2015-160918 |
| Aug. 18, 2015 | (JP) | ................................. | 2015-160920 |

(51) Int. Cl.
  *A61B 5/145* (2006.01)
  *A61B 5/1455* (2006.01)

(56) References Cited

U.S. PATENT DOCUMENTS

| 6,152,875 | A | 11/2000 | Hakamata | |
| 6,246,893 | B1* | 6/2001 | Gobeli | A61B 5/14558 |
| | | | | 600/318 |
| 2003/0225321 | A1* | 12/2003 | Cote | A61B 5/14558 |
| | | | | 600/318 |
| 2012/0307209 | A1 | 12/2012 | Glynn | |
| 2017/0042529 | A1* | 2/2017 | Shugarman | A61B 17/0231 |
| 2017/0049320 | A1* | 2/2017 | Nishizaki | A61B 3/117 |

FOREIGN PATENT DOCUMENTS

| JP | 3543923 B2 | 7/2004 |
| JP | 2013-517825 A | 5/2013 |

OTHER PUBLICATIONS

Written Opinion dated Feb. 16, 2016 issued by the International Searching Authority in counterpart International Application No. PCT/JP2015/083110 (PCT/ISA/237).

\* cited by examiner

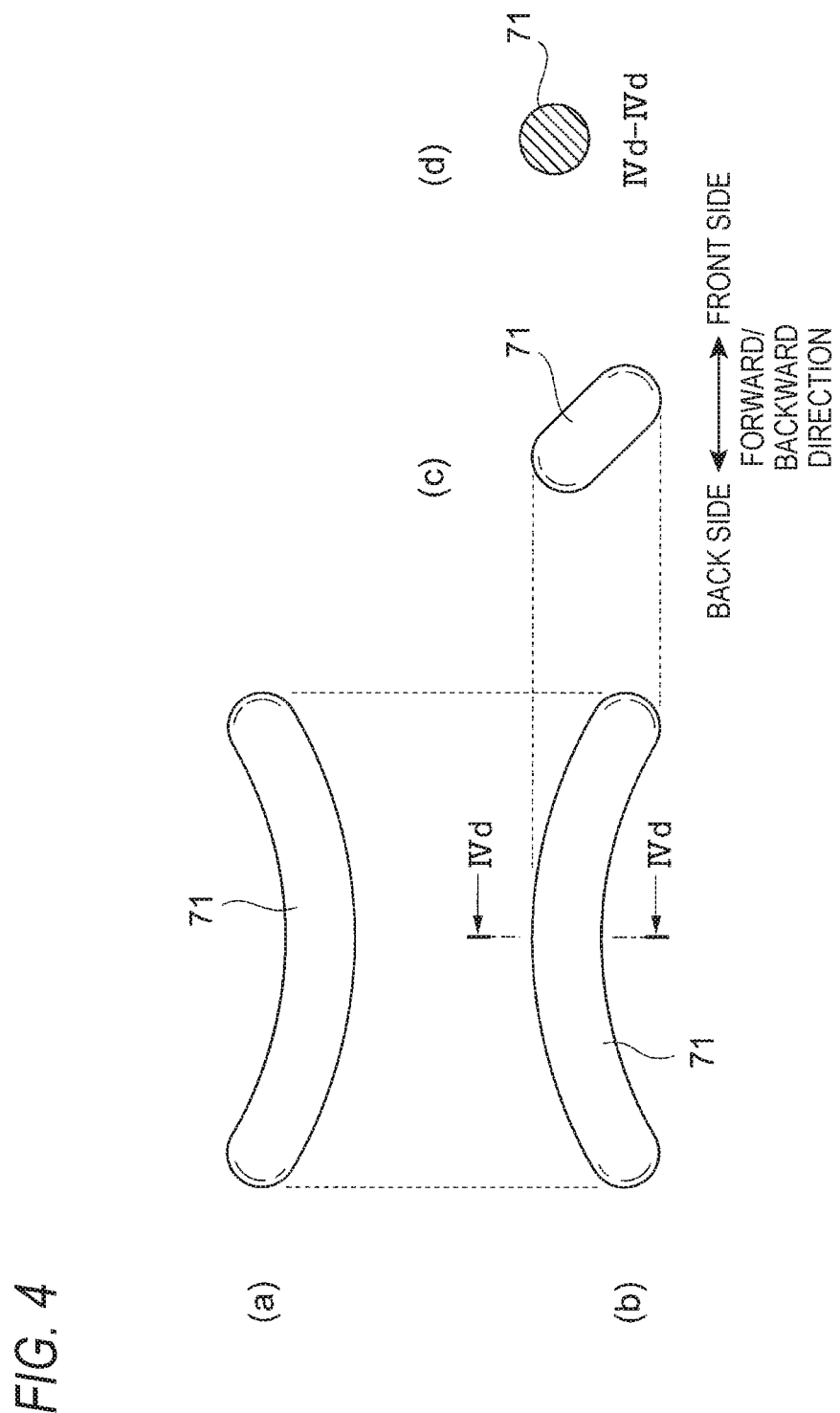

OPTICAL MEASUREMENT APPARATUS AND LIGHT IRRADIATION/RECEPTION METHOD

CROSS REFERENCE TO RELATED APPLICATION

This is a continuation of International Application No. PCT/JP2015/083110 filed on Nov. 25, 2015, and claims priority from Japanese Patent Application No. 2014-239091 filed on Nov. 26, 2014, Japanese Patent Application No. 2014-239092 filed on Nov. 26, 2014, Japanese Patent Application No. 2014-239093 filed on Nov. 26, 2014, Japanese Patent Application No. 2015-160918 filed on Aug. 18, 2015, and Japanese Patent Application No. 2015-160920 filed on Aug. 18, 2015.

BACKGROUND

Technical Field

The present invention relates to an optical measurement apparatus and a light irradiation/reception method.

SUMMARY

According to an aspect of the invention, there is provided an optical measurement apparatus including: an emission section that emits light such that the light travels across an anterior chamber of an eyeball of a measurement subject; a light reception section that receives light that is emitted from the emission section and travels across the anterior chamber; and a positioning section that performs positioning of one of the emission section and the light reception section at a position where skin on a periphery of an inner canthus of the eyeball is squeezed into an eye socket accommodating the eyeball

BRIEF DESCRIPTION OF DRAWINGS

Exemplary embodiment(s) of the present invention will be described in detail based on the following figures, wherein:

FIG. 4 illustrates the detailed configuration of the eyelid pressing section;

DETAILED DESCRIPTION

Hereinafter, with reference to the accompanying drawings, an exemplary embodiment of the present invention will be described. (optical measurement apparatus 1)

Figure 1:
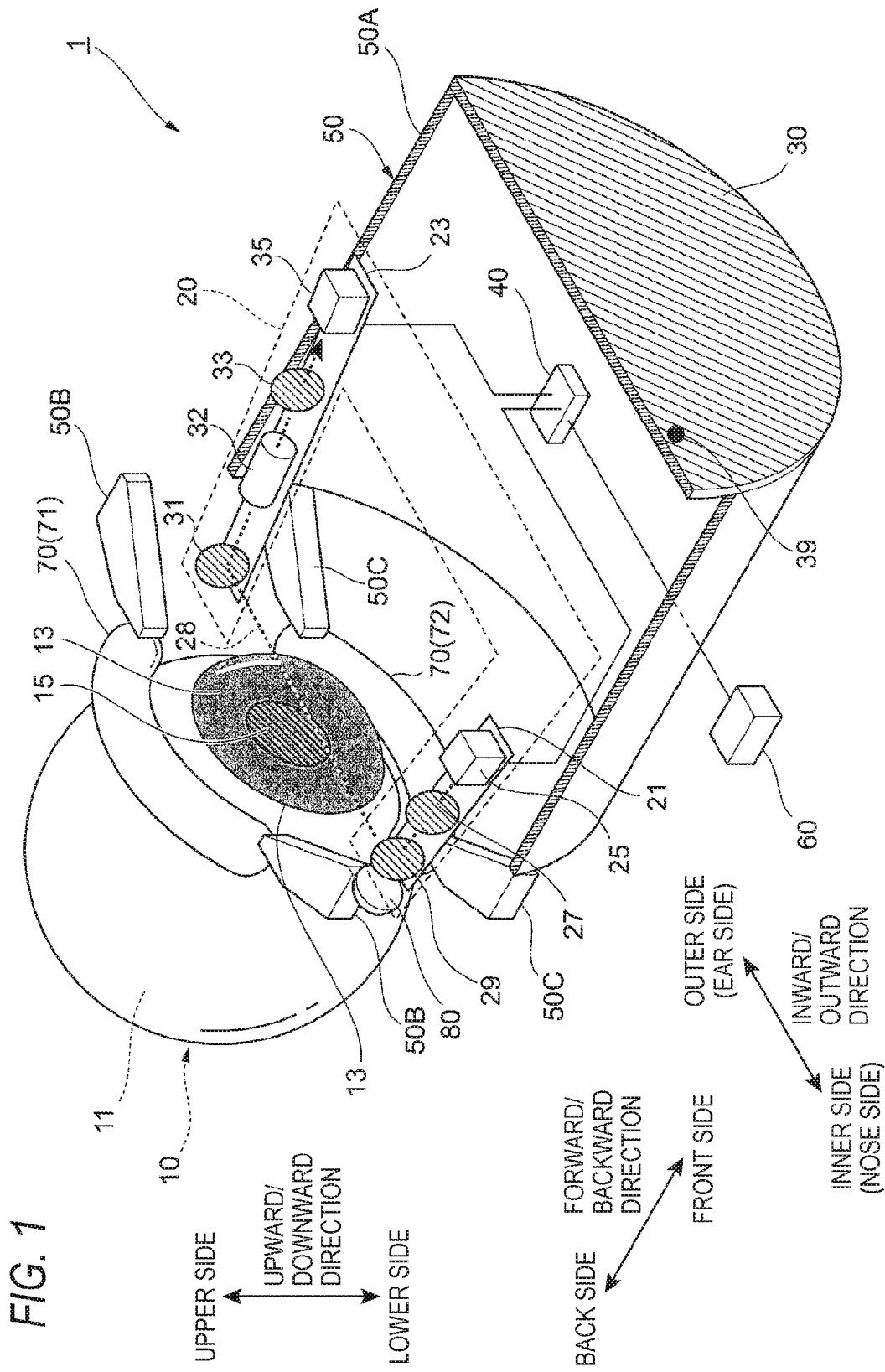
FIG. 1 illustrates an example of a configuration of an optical measurement apparatus in which the present exemplary embodiment is applied.

FIG. 1 is a view illustrating an example of a configuration of the optical measurement apparatus 1 in which the present exemplary embodiment is applied. The optical measurement apparatus 1 has a shape such that a measurement subject holds the optical measurement apparatus 1 in his/her own hand and can perform a measurement by wearing (applying) the optical measurement apparatus 1 in an eyeball 10 (on the periphery of the eyeball 10) by himself, herself. The eyeball 10 illustrated in FIG. 1 is the left eye.

The optical measurement apparatus 1 includes an optical system 20 that is used for measuring characteristics of aqueous humor in an anterior chamber 13 of the eyeball 10 of the measurement subject; a display section 30 that performs displaying for inducing a visual line of the measurement subject; a control section 40 that controls the optical system 20 and the display section 30; a holding section 50 that holds the optical system 20, the display section 30, and the control section 40; a calculation section 60 that calculates the characteristics of the aqueous humor based on data measured by using the optical system 20; an eyelid pressing section 70 that comes into contact with an eyelid of the measurement subject and presses the eyelid, and an inner canthus squeezing portion 80 that squeezes an inner canthus side of the eyelid of the measurement subject.

In the description below, a direction crossing the upper side of the sheet and the lower side of the sheet regarding the optical measurement apparatus 1 illustrated in FIG. 1 is sometimes referred to as upward/downward direction. In addition, a direction crossing the front side of the measurement subject and the back side of the measurement subject illustrated in FIG. 1 is sometimes referred to as forward/backward direction. In addition, a direction crossing the inner side (nose side, inner canthus side) and the outer side (ear side, outer canthus side) when viewed from the measurement subject of the optical measurement apparatus 1 illustrated in FIG. 1 is sometimes referred to as inward/outward direction.

In addition, the characteristics of the aqueous humor measured by the optical measurement apparatus 1 in which the present exemplary embodiment is applied denotes a rotation angle (optical rotation degree $\alpha_M$) of a polarization plane of linearly polarized light caused by an optically active substance contained in the aqueous humor, a color absorbance degree (circular dichroism) with respect to circularly polarized light, and the like. The polarization plane of linearly polarized light denotes a surface where the electric field of the linearly polarized light vibrates.

The optical system 20 includes a light emission system 21 that emits light with which the anterior chamber 13 (will be described later) of the eyeball 10 is irradiated, and a light reception system 23 that receives light which has passed through the anterior chamber 13.

First, the light emission system 21 includes a light emission portion 25, a polarizer 27, and a first mirror 29.

The light emission portion 25 may be a light source having a wide wavelength width, such as a light emitting diode (LED) and a lamp or may be a light source having a narrow wavelength width, such as a laser. It is preferable that the wavelength width of the light emission portion 25 is narrow. In addition, the light emission portion 25 may emit light having two or more wavelengths.

The polarizer 27 is a Nicol prism, for example. From rays of incident light, the polarizer 27 allows linearly polarized light having a predetermined polarization plane to pass through.

It is preferable that the first mirror 29 which is an example of an emission portion causes an optical path 28 to be refracted and maintains linearly polarized light without any change before and after reflection. In a case where there is no need for the optical path 28 to be refracted, the first mirror 29 may not be provided.

Subsequently, the light reception system 23 includes a second mirror 31, a compensator 32, an analyzer 33. and a light reception portion 35.

It is preferable that the second mirror 31 which is an example of a light reception portion is similarly configured as the first mirror 29, causes the optical path 28 to be refracted, and maintains linearly polarized light without any change before and after reflection. In a case where there is no need for the optical path 28 to be refracted, the second mirror 31 may not be provided.

For example, the compensator 32 is a magneto-optic element such as a Faraday element in which a garnet or the like is used. The compensator 32 rotates the polarization plane of linearly polarized light in response to a magnetic field.

The analyzer 33 is a member similar to the polarizer 27 and allows linearly polarized light having the predetermined polarization plane to pass through.

The light reception portion 35 is a light receiving element such as a silicon diode and outputs an output signal corresponding to the intensity of light.

The display section 30 has a display which electronically displays an image. The display section 30 induces the orientation of (visual line) of the eyeball 10 in a predetermined direction by displaying a mark (target) 39 which the measurement subject may visually recognize. The display section 30 displays an image of predetermined information such as the characteristics of the aqueous humor (concentration of the optically active substance, and the like) calculated by the calculation section 60.

The control section 40 controls the light emission portion 25, the compensator 32, the light reception portion 35, and the like in the optical system 20, thereby obtaining measurement data related to the characteristics of the aqueous humor. In addition, the control section 40 causes the display section 30 to display the mark 39.

The holding section 50 is an approximately cylindrical housing which holds the optical system 20 and the control section 40, and has a shape such that the measurement subject holds the holding section 50 in his/her own hand and may wear (apply) the holding section 50 in the eyeball 10 of himself/herself. The holding section 50 illustrated in FIG. 1 exhibits a shape realized by cutting a cylinder along a plane parallel to an axial direction such that the optical system 20 is easily recognized. In addition, the shape of the holding section 50 may be a different shape. For example, a cross section may have a quadrangular or elliptic tube shape. In addition, in the cylindrical housing, the bottom surface on a side opposite to the side to be worn may be open or may be blocked by a different member.

The calculation section 60 receives measurement data from the control section 40 and calculates the characteristics of the aqueous humor.

The eyelid pressing section 70 which is an example of a restraint portion is provided in the holding section 50 and presses eyelids (upper eyelid 18 and lower eyelid 19, refer to FIG. 3B described below) by coming into contact with the eyelids, thereby maintaining the eyelids in an open state. The configuration of the eyelid pressing section 70 will be described later.

The inner canthus squeezing portion 80 which is an example of a squeezing portion is provided in the holding section 50 and squeezes the eyelid toward the inward side. The configuration of the inner canthus squeezing portion 80 will be described later.

(Measurement of Aqueous Humor)

Subsequently, an example of measuring the aqueous humor in the anterior chamber 13 and calculating a glucose concentration of the aqueous humor by using the optical measurement apparatus 1 will be described.

The amount of injecting insulin to a diabetic patient is controlled depending on the glucose concentration in blood. Thus, it is required for the diabetic patient to grasp the glucose concentration in blood at all times. As a method of measuring the glucose concentration in blood, there is a method in which a fingertip or the like is punctured with an injection needle and a very small quantity of blood is gathered. However, in this method, even in a case of a very small quantity of blood, the diabetic patient feels pain when collecting blood, thereby accompanying a mental burden. Accordingly, there is a high demand for a noninvasive-type test method replacing an invasive-type test method such as puncturing.

Here, the aqueous humor in the anterior chamber 13 having substantially the same component as that of blood serum contains protein, glucose, ascorbic acid, and the like. It is known that there is a correlationship between the glucose concentration in blood and the glucose concentration in the aqueous humor. Moreover, in the aqueous humor, generally, there is no cell substance of blood, and there is small influence of light scattering. Protein, glucose, ascorbic acid, and the like contained in the aqueous humor are the optically active substances and have optical activities.

In the optical measurement apparatus 1 in which the present exemplary embodiment is applied, while the aqueous humor is utilized, the concentration of glucose or the like having the optical activities is optically measured.

(Setting Optical Path)

In a technique of optically measuring the concentration or the like of the optically active substances such as glucose contained in the aqueous humor, as optical paths which can be set, there are two optical paths as follows.

In one optical path being different from the configuration illustrated in FIG. 1, light is incident at an angle nearly perpendicular to the eyeball 10, that is, along the forward/backward direction, the light is reflected by the interface between a cornea 14 (refer to FIG. 6) and the aqueous humor or the interface between the aqueous humor and a crystalline lens 12, and the reflected light is received (detected). In the other optical path as in the configuration illustrated in FIG. 1, light is incident at an angle intersecting the forward/backward direction, specifically at an angle nearly parallel to the eyeball 10, and the light which has passed through the aqueous humor in the anterior chamber 13 is received (detected).

Figure 6:
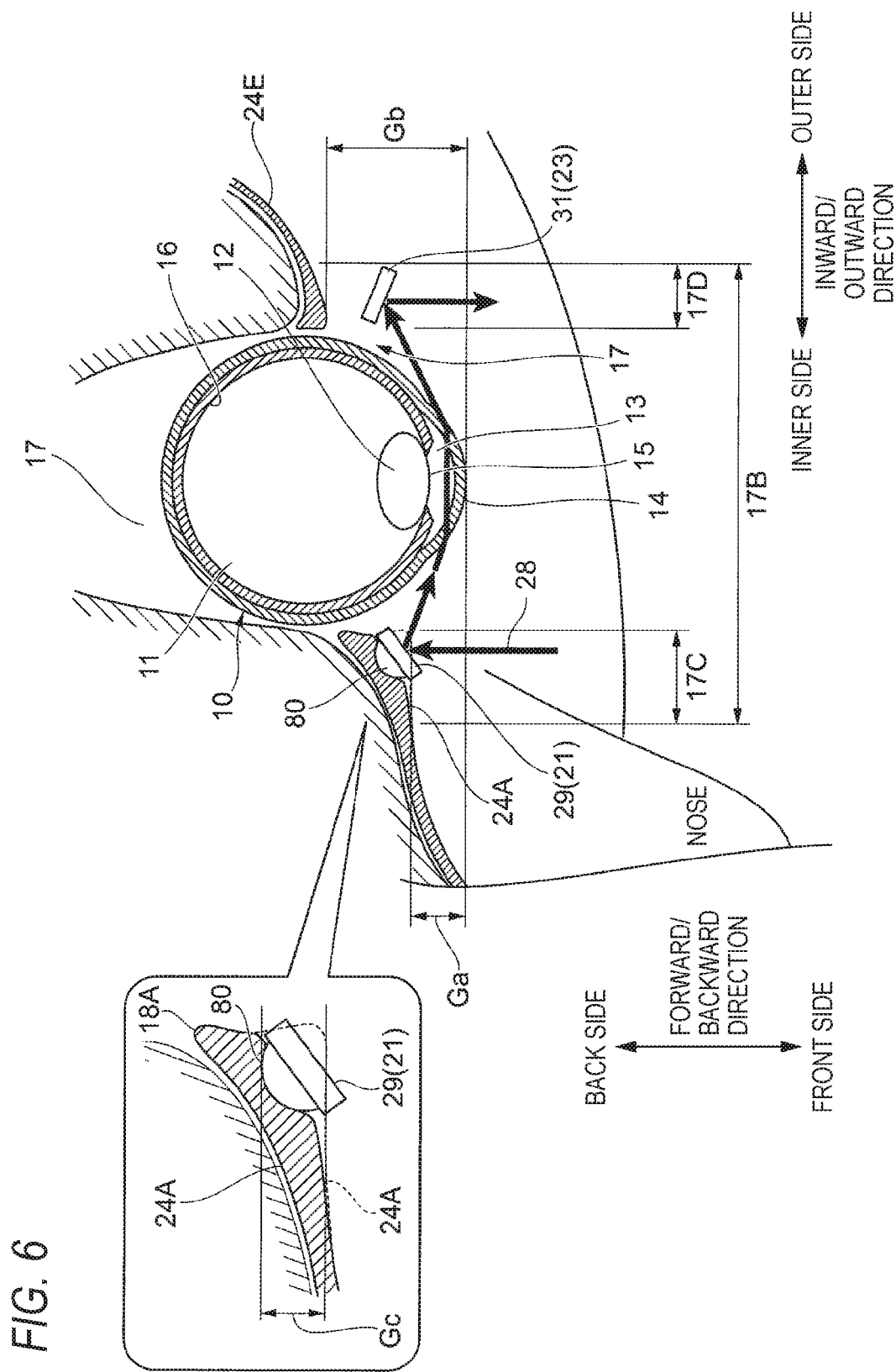
FIG. 6 describes operations of the eyelid pressing section and the inner canthus squeezing portion.

In an optical path such as the former above in which light is incident at an angle nearly perpendicular to the eyeball 10, there is a possibility that the light reaches the retina 16 (refer to FIG. 6). Particularly, in a case of using a laser having high coherency in the light emission portion 25, it is not preferable when light reaches the retina 16.

In contrast, in the optical path 28 such as the latter above in which light is incident at an angle nearly parallel to the eyeball 10, the light passes through the anterior chamber 13 so as to travel across the anterior chamber 13 via the cornea 14, and the light which has passed through the aqueous humor is received (detected). Therefore, the light is restrained from reaching the retina 16.

(Calculation of Concentration of Optically Active Substance)

Figure 2:
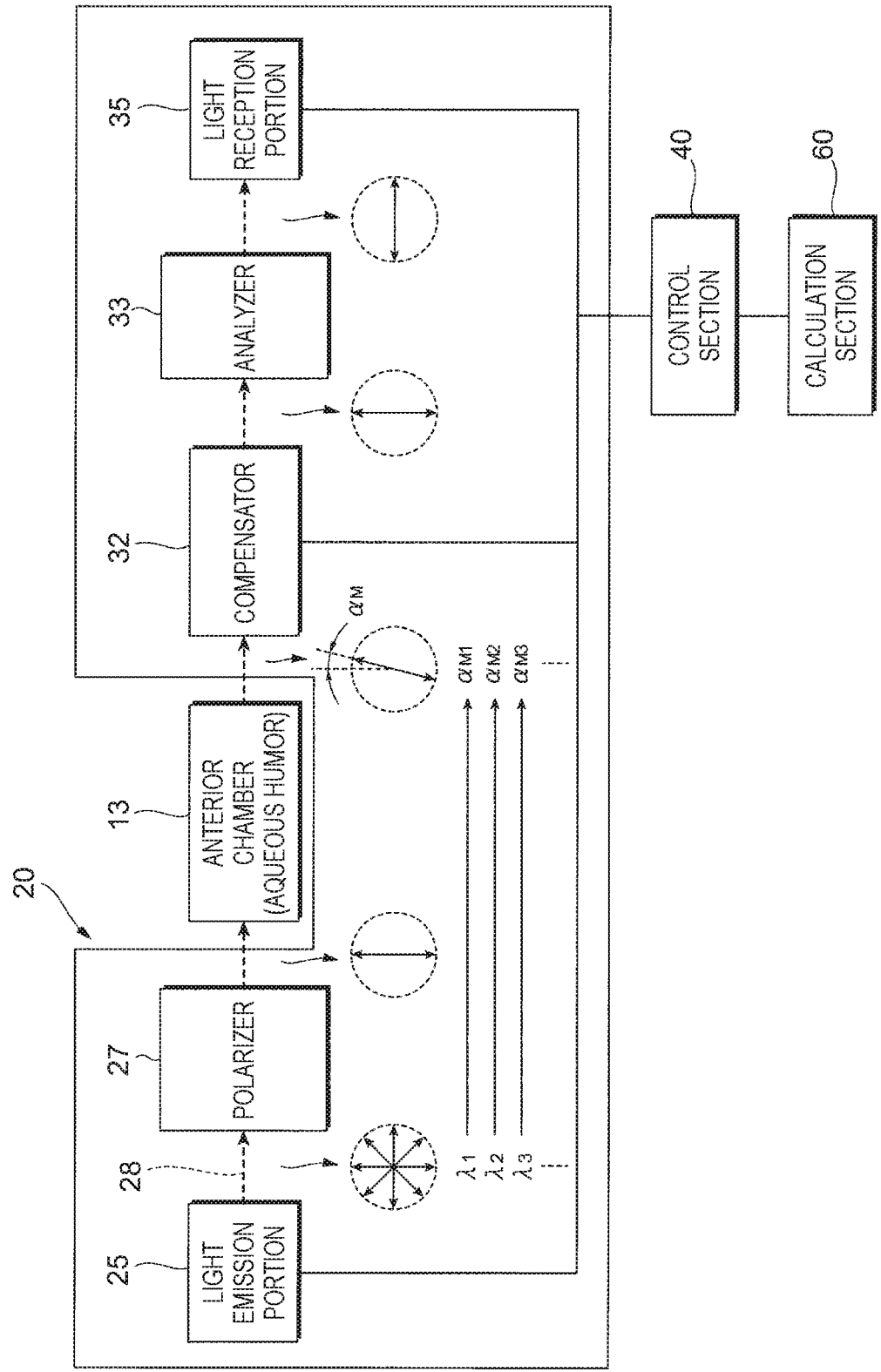
FIG. 2 describes a method of measuring a rotation angle of a polarization plane caused by an optically active substance contained in aqueous humor in an anterior chamber, by using the optical measurement apparatus.

FIG. 2 is a view describing a method of measuring the rotation angle (optical rotation degree) of the polarization plane caused by the optically active substance contained in the aqueous humor in the anterior chamber 13, by using the optical measurement apparatus 1. Here, in order to make description easy, the optical path 28 is configured not to be refracted (to be linear), and illustration of the first mirror 29 and the second mirror 31 is omitted.

In addition, in each of the spaces among the light emission portion 25, the polarizer 27, the anterior chamber 13, the compensator 32, the analyzer 33, and the light reception portion 35 illustrated in FIG. 2, the states of polarized light viewed in traveling directions of the light are respectively indicated with arrows in a circle.

The light emission portion 25 emits light having a random polarization plane. The polarizer 27 allows linearly polarized light having the predetermined polarization plane to pass through. In FIG. 2, as an example, linearly polarized light having the polarization plane parallel to the sheet passes through.

The polarization plane of the linearly polarized light which has passed through the polarizer 27 is rotated due to the optically active substance contained in the aqueous humor in the anterior chamber 13. In FIG. 2, the polarization plane rotates by the angle $\alpha_M$ (optical rotation degree $\alpha_M$).

Subsequently, a magnetic field is applied to the compensator 32 such that the polarization plane rotated due to the optically active substance contained in the aqueous humor in the anterior chamber 13 returns to the original state.

The linearly polarized light which has passed through the analyzer 33 is received by the light reception portion 35 and is converted into an output signal corresponding to the intensity of light.

Here, an example of the method of measuring the optical rotation degree $\alpha_M$ by using the optical system 20 will be described.

First, in a state where light emitted from the light emission portion 25 is prohibited from passing through the anterior chamber 13, while the optical system 20 including the light emission portion 25, the polarizer 27, the compensator 32, the analyzer 33, and the light reception portion 35 is used, the compensator 32 and the analyzer 33 are set such that an output signal of the light reception portion 35 is minimized. In the example illustrated in FIG. 2, in a state where light is prohibited from passing through the anterior chamber 13, the polarization plane of the linearly polarized light which has passed through the polarizer 27 becomes orthogonal to the polarization plane passing through the analyzer 33.

Subsequently, a state where light passes through the anterior chamber 13 is established. Then, the polarization plane rotates due to the optically active substance contained in the aqueous humor in the anterior chamber 13. Therefore, the output signal from the light reception portion 35 deviates from the minimum value. A magnetic field to be applied to the compensator 32 is set such that the output signal from the light reception portion 35 is minimized. That is, the polarization plane is rotated by the compensator 32 so as to be orthogonal to the polarization plane passing through the analyzer 33.

The angle of the polarization plane rotated by the compensator 32 corresponds to the optical rotation degree $\alpha_M$ caused by the optically active substance contained in the aqueous humor. Here, the relationship between the magnitude of the magnetic field applied to the compensator 32 and the angle of the rotated polarization plane is known in advance. Therefore, based on the magnitude of the magnetic field applied to the compensator 32, the optical rotation degree $\alpha_M$ is ascertained.

Specifically, rays of light having plural wavelengths $\lambda$ (wavelengths $\lambda_1$, $\lambda_2$, $\lambda_3$, and so on) are incident on the aqueous humor in the anterior chamber 13 from the light emission portion 25, and the optical rotation degrees $\alpha_M$ (optical rotation degrees $\alpha_{M1}$, $\alpha_{M2}$, $\alpha_{M3}$, and so on) are respectively obtained with respect to the wavelengths. The sets of the wavelength $\lambda$ and the optical rotation degree $\alpha_M$ are taken into the calculation section 60, and the concentration of an intended optically active substance is calculated.

The concentration of the optically active substance calculated by the calculation section 60 may be displayed through the display section 30 included in the optical measurement apparatus 1 or may be output to a different terminal device (not illustrated) such as a personal computer (PC) via an output section (not illustrated) included in the optical measurement apparatus 1.

Furthermore, as described above, the aqueous humor contains plural optically active substances. Thus, the measured optical rotation degree $\alpha_M$ is the sum of each of the optical rotation degrees $\alpha_M$ of the plural optically active substances. Therefore, the concentration of the intended optically active substance is required to be calculated from the measured optical rotation degree $\alpha_M$. For example, the concentration of the intended optically active substance can be calculated by using a known method such as that disclosed in JP-A-09-138231. Thus, description will be omitted herein.

In addition, in FIG. 2, both the polarization plane of the polarizer 27 and the polarization plane before passing through the analyzer 33 are parallel to the sheet. However, in a case where the polarization plane is rotated by the compensator 32 in advance, the polarization plane before passing through the analyzer 33 may incline from a plane parallel to the sheet. That is, in a state where light does not pass through the aqueous humor in the anterior chamber 13, it is favorable to set the compensator 32 and the analyzer 33 such that the output signal of the light reception portion 35 is minimized.

In addition, here, an example of using the compensator 32 is described as a method of obtaining the optical rotation degree $\alpha_M$. However, the optical rotation degree $\alpha_M$ may be obtained by using a portion other than the compensator 32. Moreover, here, an orthogonal polarizer method (however, the compensator 32 is used) which is the most basic measurement method of measuring the rotation angle (optical rotation degree $\alpha_M$) of the polarization plane is described. However, other measurement methods such as a rotation analyzer method, a Faraday modulation method, and an optical delay modulation method may be applied.

(Structures of Eyelid Pressing Section 70 and Inner Canthus Squeezing Portion 80)

Figure 3A:
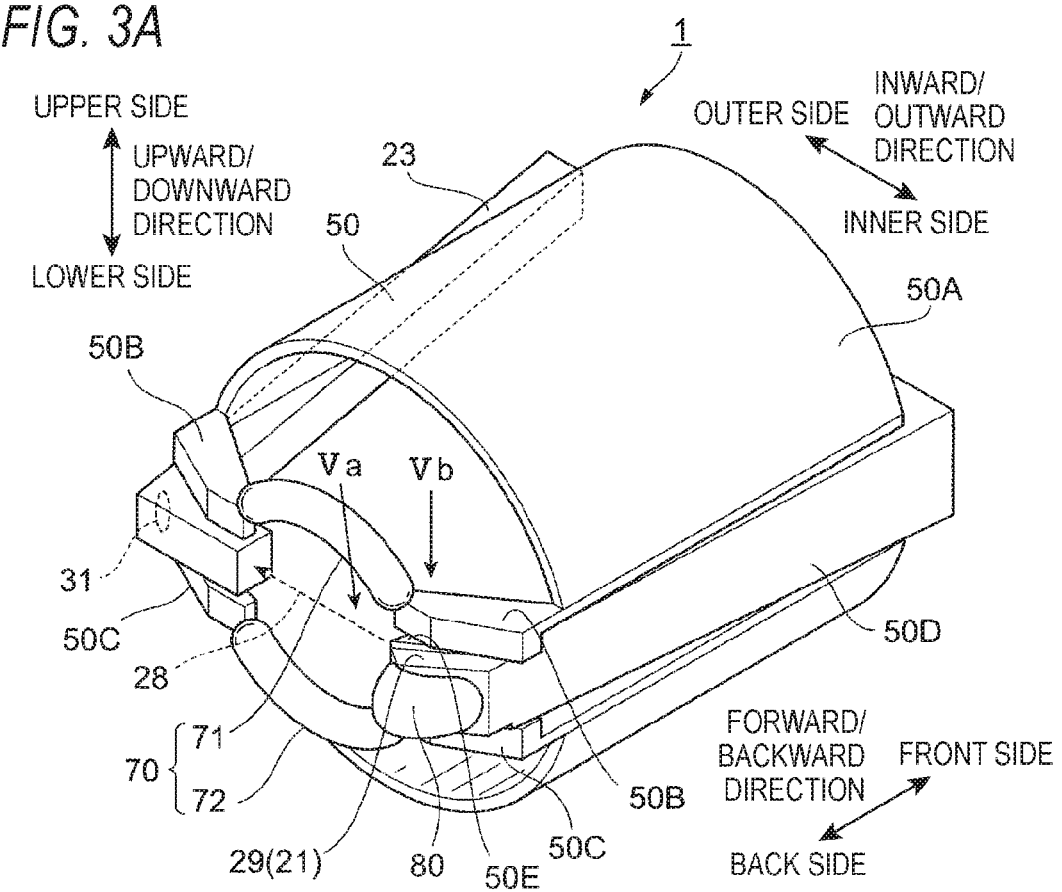
FIGS. 3A and 3B describe schematic configurations of an eyelid pressing section and an inner canthus squeezing portion.
Figure 3B:
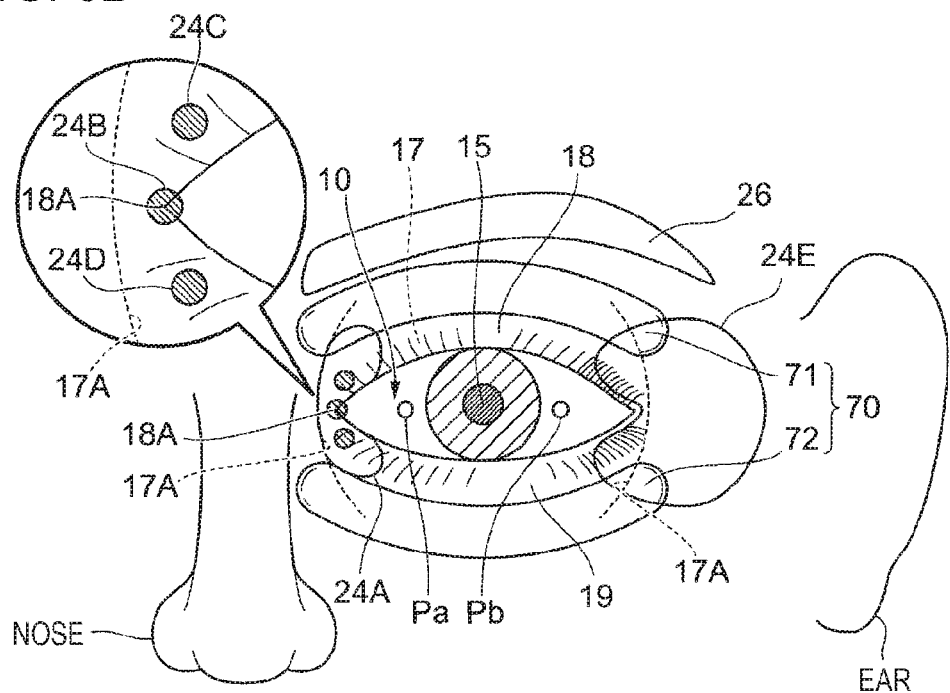

FIGS. 3A and 3B are views describing schematic configurations of the eyelid pressing section 70 and the inner canthus squeezing portion 80. More specifically, FIG. 3A is a perspective view of the optical measurement apparatus 1 viewed from the back side, and FIG. 3B is a view describing a positional relationship between the eyelid pressing section 70 and the inner canthus squeezing portion 80, and the eyelids of the measurement subject.

In addition, in (a), (b), (c) and (d) in FIG. 4 the detailed configuration of the eyelid pressing section 70 is illustrated. More specifically, (a) in FIG. 4 is a top view of an upper eyelid pressing section 71, (b) in FIG. 4 is a front view of the upper eyelid pressing section 71, (d) in FIG. 4 is a side view of the upper eyelid pressing section 71, and (d) in FIG. 4 is a cross-sectional view taken along line IVd-IVd in (b) in FIG. 4.

Figure 5A:
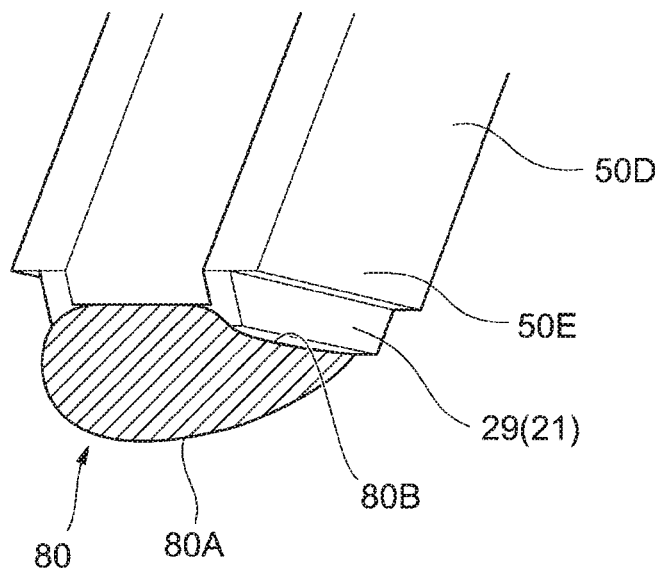
FIGS. 5A and 5B describe the detailed configuration of an upper eyelid pressing section.
Figure 5B:
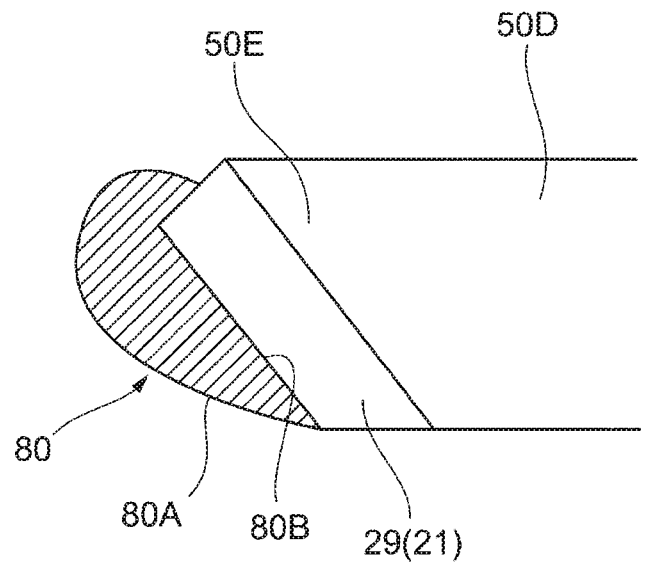

In addition, FIGS. 5A and 5B are views describing the detailed configuration of the upper eyelid pressing section 71. More specifically, FIG. 5A is a configuration diagram on the periphery of the inner canthus squeezing portion 80 viewed along the arrow Va in FIG. 3A, and FIG. 5B is a configuration diagram on the periphery of the inner canthus squeezing portion 80 viewed along the arrow Vb in FIG. 3A.

Subsequently, with reference to FIGS. 3A, 3B, 4, 5A, and 5B, disposition of the light emission system 21 and the light reception system 23, and the eyelid pressing section 70 and the inner canthus squeezing portion 80 will be described.

First, when light which has passed through the aqueous humor is detected and measures the concentration of glucose or the like by using the optical measurement apparatus 1, for example, there is a need to ensure an appropriate optical path 28 such that light is not refracted in an unintended direction and the light is not blocked by the eyelids or the like of the measurement subject. Here, as a configuration in which the optical path 28 is not blocked by the eyelids of the measurement subject, it is possible to consider a configuration in which the light emission system 21 and the light reception system 23 are respectively disposed at regions Pa and Pb overlapping the white part (sclera) of the eyeball 10 in a case of being viewed from the front. However, in this configuration, in a case where the light emission system 21 or the light reception system 23 is positionally misaligned to the inward side (back side) with respect to the eyeball 10, there is a possibility that the light emission system 21 or the light reception system 23 comes into contact with the white part of eye.

The optical measurement apparatus 1 according to the present exemplary embodiment is configured such that the light emission system 21 and the light reception system 23 are prohibited from coming into contact with the white part of eye and an appropriate optical path 28 is ensured even in a case where the light emission system 21 and the light reception system 23 are positionally misaligned in the forward/backward direction.

Specifically, in a case where the eyeball 10 is viewed from the front, the holding section 50 holds the light emission system 21 and the light reception system 23 such that the light emission system 21 or the light reception system 23 are positioned at positions respectively overlapping skin 24A on the periphery of an inner canthus or skin 24E on the periphery of an outer canthus illustrated in FIG. 3B.

In addition, as illustrated in FIG. 3A, the optical measurement apparatus 1 according to the present exemplary embodiment includes the eyelid pressing section 70 which presses the eyelids of the measurement subject, and the inner canthus squeezing portion 80 which squeezes the skin 24A on the periphery of the inner canthus of the measurement subject.

The eyelid pressing section 70 and the inner canthus squeezing portion 80 are provided at the end portion of the holding section 50 on the back side. Here, the inner canthus squeezing portion 80 protrudes to the back side beyond the eyelid pressing section 70. Specifically, in the illustrated example, the inner canthus squeezing portion 80 is disposed at a position protruding to the backmost side in the optical measurement apparatus 1.

Hereinafter, each of the specific configurations of the eyelid pressing section 70 and the inner canthus squeezing portion 80 will be described in order.

(Structure of Eyelid Pressing Section 70)

First, the eyelid pressing section 70 will be described.

As illustrated in FIG. 3A, the eyelid pressing section 70 includes the upper eyelid pressing section 71 and a lower eyelid pressing section 72. The upper eyelid pressing section 71 and the lower eyelid pressing section 72 are respectively disposed on the upper side and the lower side beyond the light emission system 21 and the light reception system 23. In other words, the upper eyelid pressing section 71 and the lower eyelid pressing section 72 are provided face to face while interposing the optical path 28 therebetween.

For example, the eyelid pressing section 70 is formed of a so-called elastic member such as a silicone resin (silicone) so as to improve wearing feeling for the measurement subject.

Here, as illustrated in FIG. 3A, the upper eyelid pressing section 71 and the lower eyelid pressing section 72 are supported by the holding section 50. Specifically, the upper eyelid pressing section 71 and the lower eyelid pressing section 72 are fixedly provided at the end portion of a cylindrical main body 50A on the back side and are respectively supported by an upper support portion 50B and a lower support portion 50C extending along the optical path 28.

Furthermore, if the upper eyelid pressing section 71, the lower eyelid pressing section 72, the light emission system 21, and the light reception system 23 are intended to be individually disposed as separate bodies in a limited space on the periphery of the eyeball 10 where the nose, the eyelashes, and the like are present, interference is likely to occur among the members. Therefore, as in the illustrated example, when the members are integrally supported by the holding section 50, each of the members is easily disposed in the limited space.

In addition, as illustrated in FIG. 3B, the upper eyelid pressing section 71 and the lower eyelid pressing section 72 are provided at positions respectively face to face with the upper eyelid 18 and the lower eyelid 19 in the holding section 50. When the upper eyelid pressing section 71 and the lower eyelid pressing section 72 are pressed against the upper eyelid 18 and the lower eyelid 19, the upper eyelid 18 and the lower eyelid 19 are in a state where movement thereof is restricted.

Subsequently, by using FIG. 4, the shapes of the upper eyelid pressing section 71 and the lower eyelid pressing section 72 will be described. Here, description is given by using the upper eyelid pressing section 71. The upper eyelid pressing section 71 and the lower eyelid pressing section 72 are symmetric to each other while having a plane as the reference in which the upward/downward direction indicates the normal line (refer to FIG. 3B).

First, as illustrated in (a) in FIG. 4, the upper eyelid pressing section 71 is a rod-like member (substantially columnar member) having a circularly-shaped cross section (refer to (d) in FIG. 4). In addition, the outer circumferential surface of the upper eyelid pressing section 71 which comes into contact with the eyelids is formed so as to have a smoothly continuous curve surface, and no corner portion is formed on the outer circumferential surface thereof.

The upper eyelid pressing section 71 is provided so as to have a shape along the upper eyelid 18 (refer to FIG. 3B), that is, so as to be curved along the eyeball 10 (refer to FIG. 3B). Specifically, as illustrated in (a), (b), (c) in FIG. 4, a central portion in the longitudinal direction is curved in the orientation protruding to the front side and in the orientation protruding to the upper side. As illustrated in FIG. 3A, the upper eyelid pressing section 71 and the lower eyelid pressing section 72 are disposed such that the central sides thereof in the inward/outward direction are curved in the orientation of being separated from each other.

(Structure of Inner Canthus Squeezing Portion 80)

Subsequently, the inner canthus squeezing portion 80 will be described.

First, as illustrated in FIG. 3A, the inner canthus squeezing portion 80 is supported by the holding section 50. More specifically, the inner canthus squeezing portion 80 is fixed to the light emission system 21 (first mirror 29) held by a light emission system holding section 50D (will be described later). Here, including the eyelid pressing section 70, the inner canthus squeezing portion 80 and the light emission system holding section 50D are examples of a positioning portion which performs positioning of the light emission system 21 and the light reception system 23 with respect to the eyeball 10. Furthermore, the inner canthus squeezing portion 80, the light emission system holding section 50D, and the eyelid pressing section 70 are supported by the holding section 50 under a positional relationship in which in a case where the optical measurement apparatus 1 is pressed toward the eyeball 10, the light emission system 21 (or the light reception system 23) is desirably disposed with respect to the eyeball 10. For example, the inner canthus squeezing portion 80 is formed of a so-called elastic member such as a silicone resin (silicone) so as to improve wearing feeling for the measurement subject. In other words, the inner canthus squeezing portion 80 is formed of a member softer than the first mirror 29 or the light emission system holding section (holding section) 50D.

In the illustrated example, the light emission system holding section 50D is a substantially rectangular parallelepiped of which the longitudinal direction is along the forward-backward direction. The light emission system holding section 50D is a member which holds each of the optical members (the light emission portion 25, the polarizer 27, and the first mirror 29, refer to FIG. 1) configuring the light emission system 21.

In addition, the light emission system holding section 50D has an end portion (protrusion portion) 50E on the back side protruding to the back side beyond the upper eyelid pressing section 71 and the lower eyelid pressing section 72, and the first mirror 29 is held by the end portion 50E on the back side.

The inner canthus squeezing portion 80 is fixed to a surface of the first mirror 29 on the back side by using a known fixing method such as an adhesive (not illustrated). Furthermore, the first mirror 29 in the illustrated example is directly pressed against the measurement subject via the inner canthus squeezing portion 80.

Here, the inner canthus squeezing portion 80 is provided so as to be integrated with the first mirror 29 which is an optical member positioned on the backmost side in the light emission system 21.

In this manner, when the inner canthus squeezing portion 80 is provided in the first mirror 29, each of the members is easily disposed in the limited space. Specifically, compared to a configuration in which the inner canthus squeezing portion 80 and the first mirror 29 are separated from each other, the first mirror 29 is more easily disposed on the inward side (back side). In addition, compared to the configuration in which the inner canthus squeezing portion 80 and the first mirror 29 are separated from each other, the first mirror 29 (light emission system holding section 50D) is restrained from coming into contact with the nose and positioning of the optical measurement apparatus 1 (refer to FIG. 3A) is restrained from being hindered. Moreover, as the skin is squeezed by the inner canthus squeezing portion 80, the first mirror 29 is also positioned at the same time.

Here, disposition of the inner canthus squeezing portion 80 will be described.

As illustrated in FIG. 3B, the inner canthus squeezing portion 80 is provided between the upper eyelid pressing section 71 and the lower eyelid pressing section 72 in the upward/downward direction, that is, at a position face to face with the inner canthus side of the upper eyelid 18 and the lower eyelid 19. Here, the inner canthus side of the upper eyelid 18 and the lower eyelid 19 denotes a part on the inner side (nose side) beyond a pupil 15 in the upper eyelid 18 and the lower eyelid 19. In addition, when viewed from another viewpoint, the inner canthus squeezing portion 80 is positioned in a region of the skin 24A on the periphery of the inner canthus. Here, the expression "the skin on the periphery of the inner canthus" denotes skin in a range which can be squeezed toward an eye socket 17 (will be described later) on the inner side (nose side) beyond the pupil 15, that is, skin in a range which can be squeezed to the inward side (back side) beyond the position of the front side apex of the eyeball 10 in a case of being squeezed. In addition, the expression "the skin on the periphery of the outer canthus" denotes skin positioned on the outer side (ear side) beyond the pupil 15, that is, both skin in a range which can be squeezed toward the eye socket 17 and skin in a range which cannot be squeezed.

Specifically, as an example, the inner canthus squeezing portion 80 is positioned in a region on the inner canthus side of the upper eyelid 18 and the lower eyelid 19, that is, the eyeball 10 side (outer side) beyond an inner peripheral surface 17A of the eye socket 17. When viewed from another viewpoint, the inner canthus squeezing portion 80 is positioned so as to be in contact with skin 24B on the periphery of the inner canthus at substantially the same position (height) as a medial ocular angle (inner canthus) 18A in the upward/downward direction of the eyeball 10. The position of the medial ocular angle (inner canthus) 18A in the upward/downward direction of the eyeball 10 is a part where skin is positioned on the backmost side (inward side of the eyeball 10) within the skin 24A on the periphery of the inner canthus. Compared to a case of being positioned at a different position, the amount of squeezing skin is reduced. The expression "substantially the same position (height) as the medial ocular angle 18A" denotes a range of ±1 mm from the position of the medial ocular angle 18A in the upward/downward direction of the eyeball 10.

Meanwhile, at the position of the medial ocular angle 18A in the upward/downward direction, since the medial ocular angle 18A and the inner peripheral surface 17A of the eye socket 17 becomes nearest to each other in distance, depending on the shape of the inner canthus squeezing portion 80, there are cases where the region for positioning is unlikely to be ensured. In such a case, positioning may be performed such that the tip of the inner canthus squeezing portion 80 comes into contact with a position vertically deviated from the position of the medial ocular angle 18A (for example, upper side position 24C or lower side position 24D). As the inner canthus squeezing portion 80 is deviated in the upward/downward direction from the position of the medial ocular angle 18A, the medial ocular angle 18A and the inner peripheral surface 17A of the eye socket 17 are separated from each other in distance. Therefore, the region in which the inner canthus squeezing portion 80 may be positioned is widened.

The positioning place in the region of the skin 24A on the periphery of the inner canthus is not necessarily uniform at all times. For example, in consideration of the shape on the periphery of the eyeball 10 of the measurement subject, the shape of the inner canthus squeezing portion 80, the positioning accuracy, and the like, the optical measurement apparatus 1 may be configured to be positioned with the measurement subject as a whole, at a position where the optical path 28 is easily ensured.

In addition, when the inner canthus squeezing portion 80 is pressed against the skin 24A on the periphery of the inner canthus, the skin 24A on the periphery of the inner canthus is squeezed to the inward side (back side) of the eye socket 17 (details will be described later).

Subsequently, by using FIGS. 5A and 5B, the shape of the inner canthus squeezing portion 80 will be described.

As illustrated in FIGS. 5A and 5B, the inner canthus squeezing portion 80 is a member having a substantially hemispherical shape. In other words, the inner canthus squeezing portion 80 includes a convex portion 80A protruding to the back side. In addition, the inner canthus squeezing portion 80 includes a concave portion 80B along the outer shape of the first mirror 29 on a side (front side) being in contact with the first mirror 29 (refer to FIG. 3A).

The convex portion 80A is a part which comes into contact with the eyelid. In the illustrated example, the convex portion 80A is formed of a smoothly continuous curve surface (curved surface) and has no corner portion.

(Operations of Eyelid Pressing Section 70 and Inner Canthus Squeezing Portion 80)

FIG. 6 is a view describing operations of the eyelid pressing section 70 and the inner canthus squeezing portion 80. FIG. 6 illustrates a state where a cross section at the center position in the upward/downward direction of the eyeball 10 is viewed from the head side (upper side) of the measurement subject.

Subsequently, with reference to FIGS. 3A, 3B. 5A, and 5B, operations of the eyelid pressing section 70 and the inner canthus squeezing portion 80 will be described.

Here, for convenience of description, the structure of the eyeball 10 and the periphery of the eyeball will be described, and after a positional relationship between the eyeball 10 and the optical path 28 is described, specific operations of the eyelid pressing section 70 and the inner canthus squeezing portion 80 will be described.

(Structure of Eyeball 10 and Periphery of Eyeball 10)

First, the structure of the eyeball 10 and the periphery of the eyeball 10 will be described.

As illustrated in FIG. 6, the eyeball 10 has a substantially spherical outer shape and a glass body 11 is present at the center. A crystalline lens 12 playing a role as a lens is embedded in a part of the glass body 11. The anterior chamber 13 is present on the front side of the crystalline lens 12. In addition, the cornea 14 is present on the front side thereof. The peripheral portion of the crystalline lens 12 is surrounded by the iris, and the center thereof is a pupil 15. Excluding a portion being in contact with the crystalline lens 12, the glass body 11 is covered with a retina 16.

The anterior chamber 13 is a region surrounded by the cornea 14 and the crystalline lens 12, and the anterior chamber 13 is a region bulging out from the spherical shape of the eyeball 10 in a convex shape. The anterior chamber 13 has a circular shape when viewed from the front. The anterior chamber 13 is filled with the aqueous humor.

The eyeball 10 is accommodated inside the eye socket 17 which is a depression (concave portion) of the skull. In addition, the eyeball 10 is covered with the eyelids (upper eyelid 18 and lower eyelid 19).

Here, as illustrated in FIG. 6, the eye socket 17 according to the present exemplary embodiment denotes a region 17B including a region in which the skull (inner peripheral surface 17A of the eye socket 17) starts to be depressed toward the inward side (back side) of the eyeball 10 with respect to the outer surface of the skin. On the inner canthus side and the outer canthus side of the region 17B of the eye socket 17, a region 17C and a region 17D in which the distance between the outer surface of the skin and the inner peripheral surface 17A of the eye socket 17 is gradually widened are present. That is, in the region 17C on the inner canthus side and the region 17D on the outer canthus side in the region 17B of the eye socket 17, the squeezing amounts of the skin 24A on the periphery of the inner canthus and the skin 24E on the periphery of the outer canthus increase toward the inward side of the eyeball 10 beyond the skin out of the range of the region 17B of the eye socket 17.

In addition, as illustrated in FIG. 6, in general measurement subjects, the skin 24A on the periphery of the inner canthus is positioned on the front side of the skin 24E on the periphery of the outer canthus in the forward/backward direction. Thus, in a state where the eyeball 10 is oriented to the front (emmetropic state), in a case where the first mirror 29 (light emission system 21) and the second mirror 31 (light reception system 23) are positioned, depending on the measurement subject, there are cases where the skin 24A on the inner canthus side needs to be squeezed.

In the present exemplary embodiment, by utilizing that the squeezing amount of the region 17C on the inner canthus side in the region 17B of the eye socket 17 increases more toward the inward side (back side) of the eye socket 17 than the skin out of the range of the region 17B of the eye socket 17, the first mirror 29 (light emission system 21) is squeezed toward the eye socket 17. In other words, the first mirror 29 (light emission system 21) is positioned at a position where the skin 24A on the periphery of the inner canthus is squeezed toward the place between the inner peripheral surface 17A of the eye socket 17 and the eyeball 10. In this manner, in a case of a measurement in a state where the eyeball 10 is oriented toward the front (emmetropic state), even in a case where there is no (small) space for disposing the first mirror 29 (light emission system 21) due to the skin 24A on the periphery of the inner canthus, the optical path 28 traveling across the anterior chamber 13 is ensured by squeezing the skin 24A on the periphery of the inner canthus into the eye socket 17.

(Positional Relationship Between Eyeball 10 and Optical Path 28)

Subsequently, a positional relationship between the eyeball 10 and the optical path 28 of the optical system 20 will be described.

As illustrated in FIG. 6, the light emitted from the light emission system 21 is incident on the anterior chamber 13 in an orientation toward the outer side (outer canthus side) in the inward/outward direction and in an orientation toward the front side in the forward/backward direction. In addition, the light which has passed through the anterior chamber 13 is incident on the light reception system 23 in the orientation toward the outer side in the inward/outward direction and in the orientation toward the back side in the forward/backward direction.

That is, the light emission system 21 (first mirror 29) is disposed such that the light emitted toward the anterior chamber 13 by the light emission system 21 obliquely travels toward the front side in the forward/backward direction. In other words, the first mirror 29 is disposed on the back side (inward side) with respect to an exposed portion (anterior chamber 13) of the eyeball 10 closer than the front side apex thereof.

In addition, the light reception system 23 (second mirror 31) is disposed so as to receive light obliquely traveling from the anterior chamber 13 toward the back side in the forward/backward direction. In other words, the second mirror 31 is disposed on the back side beyond the front side apex of the exposed portion (anterior chamber 13) of the eyeball 10.

The disposition is performed due to the following reason. That is, light emitted from the light emission portion 25 passes through the cornea 14 and is incident on the anterior chamber 13. In this case, since the refractive index (n=approximately 1.37) of the aqueous humor in the cornea 14 and the anterior chamber 13 is greater than that of air (n=approximately 1.0) and the anterior chamber 13 and the cornea 14 have convex shapes, the optical path 28 is refracted to the back side (eyeball 10 side). In addition, even after passing through the anterior chamber 13, the optical path 28 is further refracted to the back side. In consideration of the optical path 28 passing through the cornea 14 and the anterior chamber 13 and being refracted toward the back side, the light emission system 21 and the light reception system 23 are disposed.

In addition, the nose (bridge of the nose) is positioned around the eye (eyeball 10) in the face, and there is a small space for setting the optical system 20. Moreover, when light deviates from the anterior chamber 13, accurate measurements cannot be performed. Thus, it is preferable to set the optical path 28 such that light travels across the anterior chamber 13 without deviating from the anterior chamber 13.

In addition, the optical rotation degree αM is influenced by an optical path length which is the length of light passing through the aqueous humor in the anterior chamber 13. Therefore, as described above, it is favorable to set the optical path 28 such that the optical path length does not fluctuate. In the illustrated optical measurement apparatus 1, since the optical path 28 is set so as to travel across the anterior chamber 13, an elongated optical path length may be set.

(Specific Operation of Eyelid Pressing Section 70 and Inner Canthus Squeezing Portion 80)

Subsequently, operations of the eyelid pressing section 70 and the inner canthus squeezing portion 80 will be specifically described.

First, the skin 24A on the periphery of the inner canthus is squeezed to the inward side (back side) by pressing the inner canthus squeezing portion 80 against the eyelids (upper eyelid 18 and the lower eyelid 19) of the measurement subject. Specifically, the inner canthus squeezing portion 80 squeezes the skin 24A on the periphery of the inner canthus toward the place between the inner peripheral surface 17A of the eye socket 17 and the eyeball 10.

As illustrated in FIG. 6, the length of a part of the eyeball 10 protruding with respect to the skin 24A on the periphery of the inner canthus in a state of not being squeezed, that is, a protrusion degree Ga of the eyeball 10 with respect to the skin 24A on the periphery of the inner canthus is approximately 6 mm, and a protrusion degree Gb with respect to the skin 24E on the periphery of the outer canthus ranges approximately from 11 mm to 12 mm. In addition, a movement quantity Gc of the skin 24A on the periphery of the inner canthus when being squeezed by the inner canthus squeezing portion 80 ranges approximately from 3 to 5 mm, for example, on condition that the measurement subject feels no pain. That is, the protrusion degree Ga+the movement quantity Gc with respect to the skin 24A on the periphery of the inner canthus in a state where the skin 24A on the periphery of the inner canthus is squeezed and the protrusion degree Gb with respect to the skin 24E on the periphery of the outer canthus are substantially the same as each other.

In this manner, as the inner canthus squeezing portion 80 squeezes the skin 24A on the periphery of the inner canthus, the space for disposing the first mirror 29 (light emission system 21) is more significantly ensured. That is, the first mirror 29 can be disposed on a side further to the back. Accordingly, even in a state where the eyeball 10 is oriented toward the front (emmetropic state), the optical path 28 passing through the aqueous humor in the anterior chamber 13 is easily ensured. In other words, the optical path 28 is restrained from being blocked by the upper eyelid 18 and the lower eyelid 19.

The position of the optical measurement apparatus 1 (refer to FIG. 1) worn in the measurement subject is determined by pressing the eyelid pressing section 70 (upper eyelid pressing section 71 and lower eyelid pressing section 72) against the eyelids (upper eyelid 18 and the lower eyelid 19) of the measurement subject. That is, together with the inner canthus squeezing portion 80, the light emission system holding section 50D, and the like, the eyelid pressing section 70 functions as the positioning portion with respect to the eyeball 10. In addition, when being pressed with the eyelid pressing section 70, stress acts in a direction in which the upper eyelid 18 and the lower eyelid 19 are open along the eyeball 10, and the upper eyelid 18 and the lower eyelid 19 are maintained in an open state.

Here, as the skin 24A on the periphery of the inner canthus is squeezed by the inner canthus squeezing portion 80, the eyelids tend to be closed. In other words, as the eyelids are squeezed to the inward side by the inner canthus squeezing portion 80, closing stress acts on the eyelids connected to the skin 24A on the periphery of the inner canthus. In contrast, the eyelid pressing section 70 restrains the eyelids from being closed, and the open state of the eyelids is maintained. In other words, when the skin 24A on the periphery of the inner canthus is squeezed into the eye socket 17, in response to the squeeze, stress acts in the direction in which the eyelids are closed and a region of the eyeball 10 exposed from the skin becomes narrow. Therefore, the optical path 28 passing through the aqueous humor in the anterior chamber 13 can be restricted. In the present exemplary embodiment, since the eyelid pressing section 70 restrains the exposed region of the eyeball 10 from being narrow, compared to a configuration having no eyelid pressing section 70, the optical path 28 passing through the aqueous humor in the anterior chamber 13 is easily ensured. The expression "restrain the exposed region of the eyeball 10 from being narrow" denotes that the exposed region of the eyeball 10 is in a state wider than that in the configuration having no eyelid pressing section 70 at the moment the light emission system 21 emits light, including a configuration in which the exposed region of the eyeball 10 is wider than that in a state where the skin is not squeezed.

(Adduction Measurement)

Figure 7A:
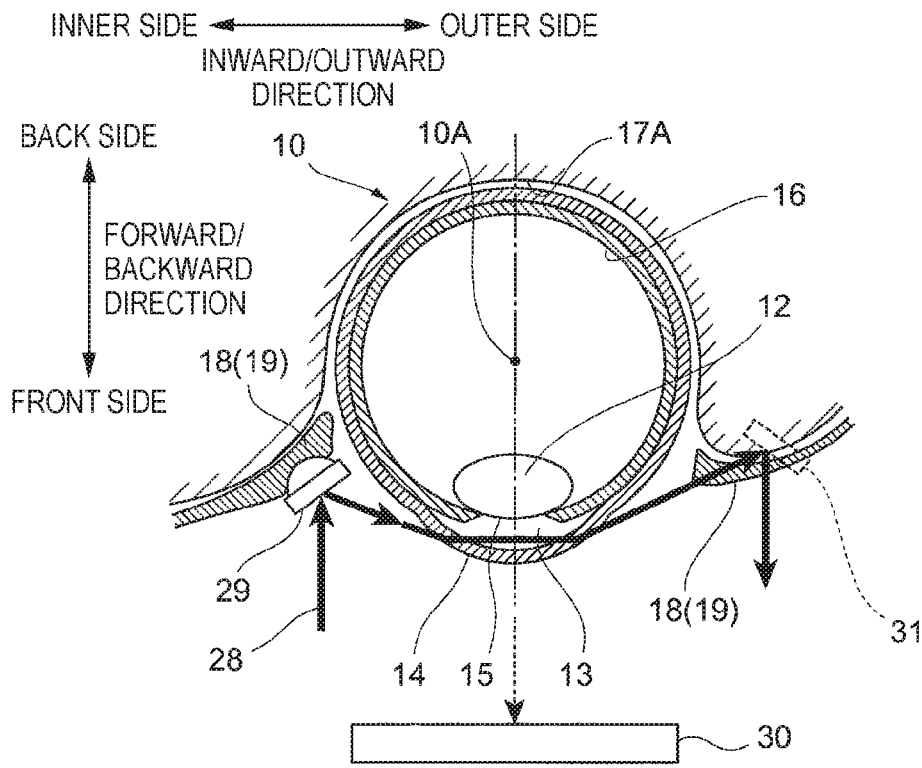
FIGS. 7A and 7B describe disposition of the optical measurement apparatus.
Figure 7B:
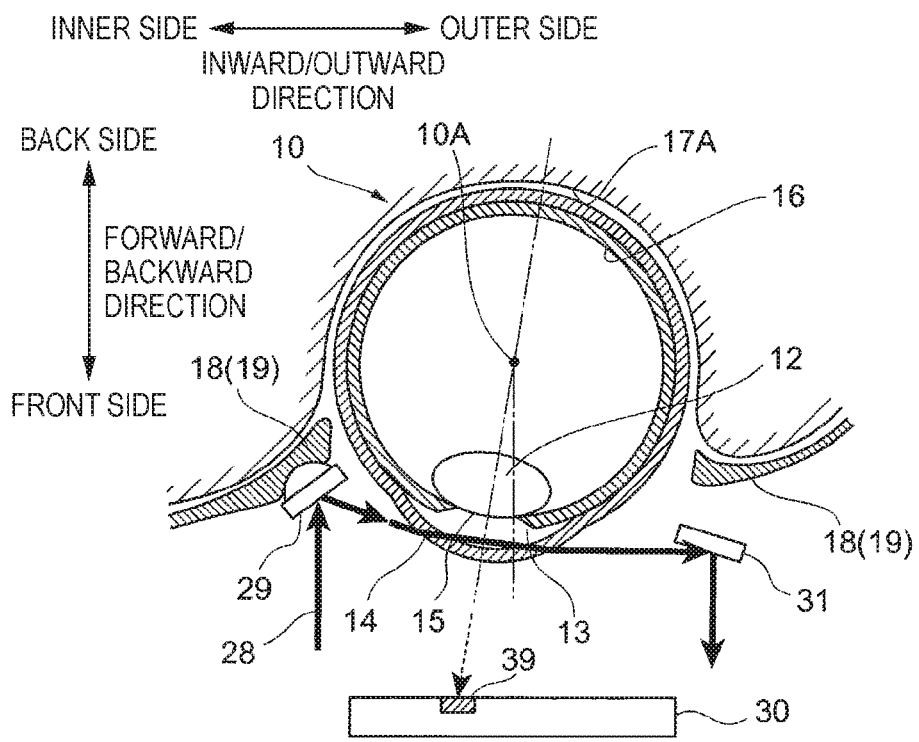

The exemplary embodiment in which a measurement is performed in a state where the eyeball 10 is adducted will be described with reference to FIGS. 7A and 7B. Here, FIG. 7A is a view describing disposition of the optical measurement apparatus 1 in a case where a measurement is performed in the emmetropic state. FIG. 7A is different from FIG. 6 in that the position of the skin 24E on the periphery of the outer canthus protrudes further to the front side in the forward/backward direction than the shape of the face in FIG. 6. FIG. 7B is a view describing disposition of the optical measurement apparatus 1 in a case where a measurement is performed in a state where the eyeball 10 is adducted. For convenience of drawing, the sizes illustrated in FIGS. 7A and 7B are different from the sizes illustrated in FIG. 6.

In a case where the eyeball 10 is viewed from the front, turning of the eyeball 10 (pupil 15) to the inner canthus side (nose side) within a range of ±45° in the upward/downward direction while having the inward/outward direction as the reference is referred to as "adduction", and turning of the eyeball 10 (pupil 15) to the outer canthus side (ear side) within a range of ±45° in the upward/downward direction while having the inward/outward direction as the reference is referred to as "abduction". Here, turning of the eyeball 10 to the inner side (nose side) while having an axis 10A as the center is an example of "adduction", and turning thereof to the outer side (ear side) while having the axis 10A as the center is an example of "abduction".

First, as illustrated in FIG. 7A, depending on the shape of the face of the measurement subject, sometimes the skin 24E on the periphery of the outer canthus protrudes further to the front side in the forward/backward direction than the shape illustrated in FIG. 6. For example, in a case where the positions of the skin 24A on the periphery of the inner canthus and the skin 24E on the periphery of the outer canthus are positions substantially the same as each other in the forward/backward direction, if the skin on the outer canthus side is not squeezed to the same extent as that on the inner canthus side, there are cases where the optical path 28 passing through the aqueous humor in the anterior chamber 13 is unlikely to be ensured in the emmetropic state.

In addition, general measurement subjects have more eyelashes on the outer canthus side than the inner canthus side. Thus, as the shape illustrated in FIG. 6, even in a case where the skin 24E on the periphery of the outer canthus is positioned on a side further to the back in the forward/backward direction than the skin 24A on the periphery of the inner canthus, there are cases where the eyelashes on the outer canthus side become an obstacle and the optical path 28 passing through the aqueous humor in the anterior chamber 13 is unlikely to be ensured in the emmetropic state.

As illustrated in FIG. 7B, in addition to squeezing the skin 24A on the periphery of the inner canthus, the eyeball 10 is adducted. In this manner, the position of the light reception system 23 (second mirror 31) disposed on the outer canthus side may be disposed on a side further to the front in the forward/backward direction of the eyeball 10 than that in the emmetropic state. That is, the light reception system 23 (second mirror 31) may be kept away to the front side in the forward/backward direction from the skin 24E on the periphery of the outer canthus or the eyelashes on the outer canthus side. Accordingly, the optical path 28 is restrained from being blocked due to the skin 24E on the periphery of the outer canthus or the eyelashes on the outer canthus side, and the optical path 28 passing through the aqueous humor in the anterior chamber 13 is easily ensured.

Specifically, as illustrated in FIG. 7B, in order to cause the eyeball 10 to be in an adducted state during a measurement, the display section 30 of the optical measurement apparatus 1 displays the mark 39. Specifically, in a case where the measurement subject is visually recognized, the mark 39 is displayed at a position where the eyeball 10 is in an adducted state. In this manner, the display section 30 displays the mark 39, for example, such that the visual line is induced so as to be oriented toward the mark 39. Then, a measurement is performed in a state where the eyeball 10 is adducted and the optical path 28 is ensured.

In the illustrated example, the second mirror 31 is disposed on a side further to the front than the first mirror 29. Accordingly, the light reception system 23 (second mirror 31) is restrained from being in contact with the measurement subject. Furthermore, pressing of the light reception system 23 (second mirror 31) is avoided and wearing feeling for the measurement subject is improved.

In addition, here, the display section 30 displays the mark 39 during a measurement. However, the mark 39 may be displayed at all times. In this case, the display section 30 may not be the display which electronically displays an image. There may be provided a member or a shape which can function as the mark 39.

Alternative Exemplary Embodiment 1

Figure 8A:
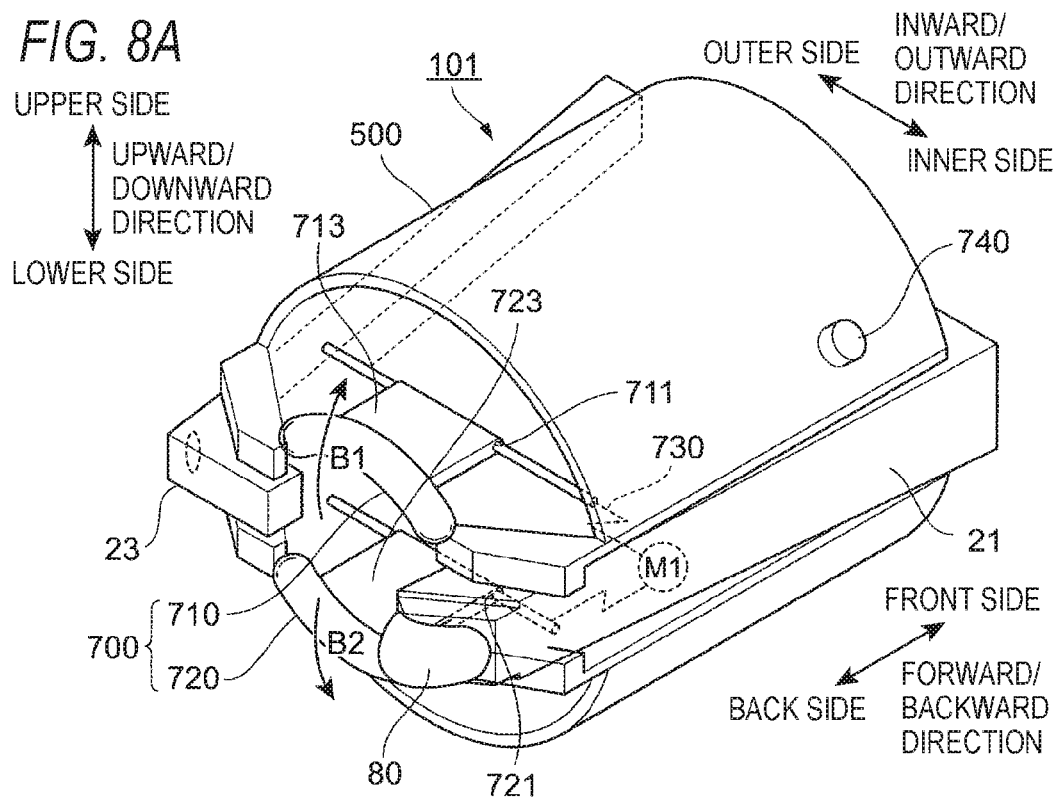
FIGS. 8A and 8B describe configurations of optical measurement apparatuses, according to alternative exemplary embodiments.
Figure 8B:
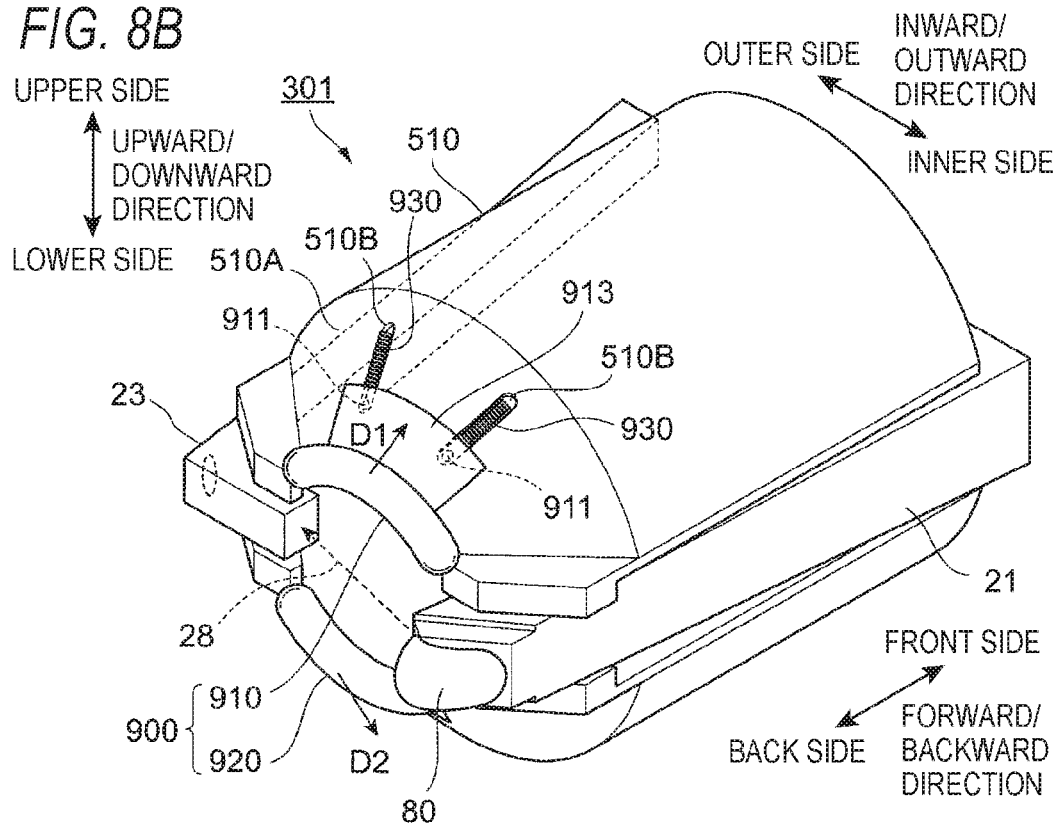

FIGS. 8A and 8B are views describing configurations of optical measurement apparatuses 101 and 301 in alternative exemplary embodiments. More specifically, FIG. 8A is a view describing a configuration of the optical measurement apparatus 101 in an alternative exemplary embodiment 1, and FIG. 8B is a view describing a configuration of the optical measurement apparatus 301 in an alternative exemplary embodiment 2.

In the above-described optical measurement apparatus 1 illustrated in FIG. 1 and the like, description is given regarding the configuration in which the position of the eyelid pressing section 70 is fixed. However, the configuration is not limited thereto. For example, as in the optical measurement apparatus 101 illustrated in FIG. 8A, an eyelid pressing section 700 (upper eyelid pressing section 710 and lower eyelid pressing section 720) may be configured to move.

Specifically, the optical measurement apparatus 101 illustrated in FIG. 8A includes a motor M1, a gear group 730 that transmits driving force from the motor M1, rotary axes 711 and 721 that extend along the inward/outward direction, and coupling members 713 and 723 that are respectively connected to the upper eyelid pressing section 710 and the lower eyelid pressing section 720. The motor M1, the gear group 730, the rotary axes 711 and 721, and the coupling members 713 and 723 are provided on the inner side of a holding section 500. In addition, the optical measurement apparatus 101 includes an operation button 740 that triggers driving of the motor M1.

An operation of the optical measurement apparatus 101 will be described.

First, the measurement subject wears the optical measurement apparatus 101 in the eyelids, and the upper eyelid pressing section 710 and the lower eyelid pressing section 720 come into contact with the upper eyelid 18 and the lower eyelid 19 (refer to FIG. 3B). In this state, for example, when the measurement subject operates the operation button 740, the motor M1 is driven. In response to the driving of the motor M1, the upper eyelid pressing section 710 and the lower eyelid pressing section 720 move in the orientation of being separated from each other (refer to arrows B1 and B2). Accordingly, the upper eyelid 18 and the lower eyelid 19 are open. In this manner, in the optical measurement apparatus 101, the eyelids can be more reliably open by driving the motor M1.

Alternative Exemplary Embodiment 2

In addition, as illustrated in FIG. 8B, a configuration in which an eyelid pressing section 900 (upper eyelid pressing section 910 and lower eyelid pressing section 920) moves by force of pressing the optical measurement apparatus 301 to the measurement subject may be applied.

Specifically, the optical measurement apparatus 301 has the below-described configuration as a mechanism of moving the upper eyelid pressing section 910. That is, the optical measurement apparatus 301 includes a truncated conical covering surface 510A which covers the back side of a holding section 510, and a guide groove 510B which is provided along the outer circumferential surface of the covering surface 510A and of which the longitudinal direction extends in the upward/downward direction. In addition, the optical measurement apparatus 301 includes a pin-like guided portion 911 which is movably provided inside the guide groove 510B, a coupling member 913 which connects the guided portion 911 and the upper eyelid pressing section 910 together, and a spring 930 which biases the coupling member 913. Here, the spring 930 biases the coupling member 913 in the orientation in which the upper eyelid pressing section 910 and the lower eyelid pressing section 920 approach each other.

In FIG. 8B, similar to the mechanism of moving the upper eyelid pressing section 910, the optical measurement apparatus 301 includes a mechanism (illustration omitted) of moving the lower eyelid pressing section 920.

An operation of the optical measurement apparatus 301 will be described.

First, the measurement subject wears the optical measurement apparatus 301 in the eyelids, and the upper eyelid pressing section 910 and the lower eyelid pressing section 920 come into contact with the upper eyelid 18 and the lower eyelid 19 (refer to FIG. 3B).

For example, when the measurement subject applies force of further pressing the optical measurement apparatus 301 to the upper eyelid 18 and the lower eyelid 19, the guided portion 911 moves inside the guide groove 510B against biasing force of the spring 930. Accordingly, the upper eyelid pressing section 910 and the lower eyelid pressing section 920 connected to the coupling member 913 move in the orientation of being separated from each other (refer to arrows D1 and D2). As a result thereof, the upper eyelid 18 and the lower eyelid 19 are open.

In this manner, in the optical measurement apparatus 301, without receiving driving force from the driving source, the measurement subject can reliably open the eyelids by utilizing the force of pressing the optical measurement apparatus 301 to the upper eyelid 18 and the lower eyelid 19.

Alternative Exemplary Embodiment 3

Figure 9:
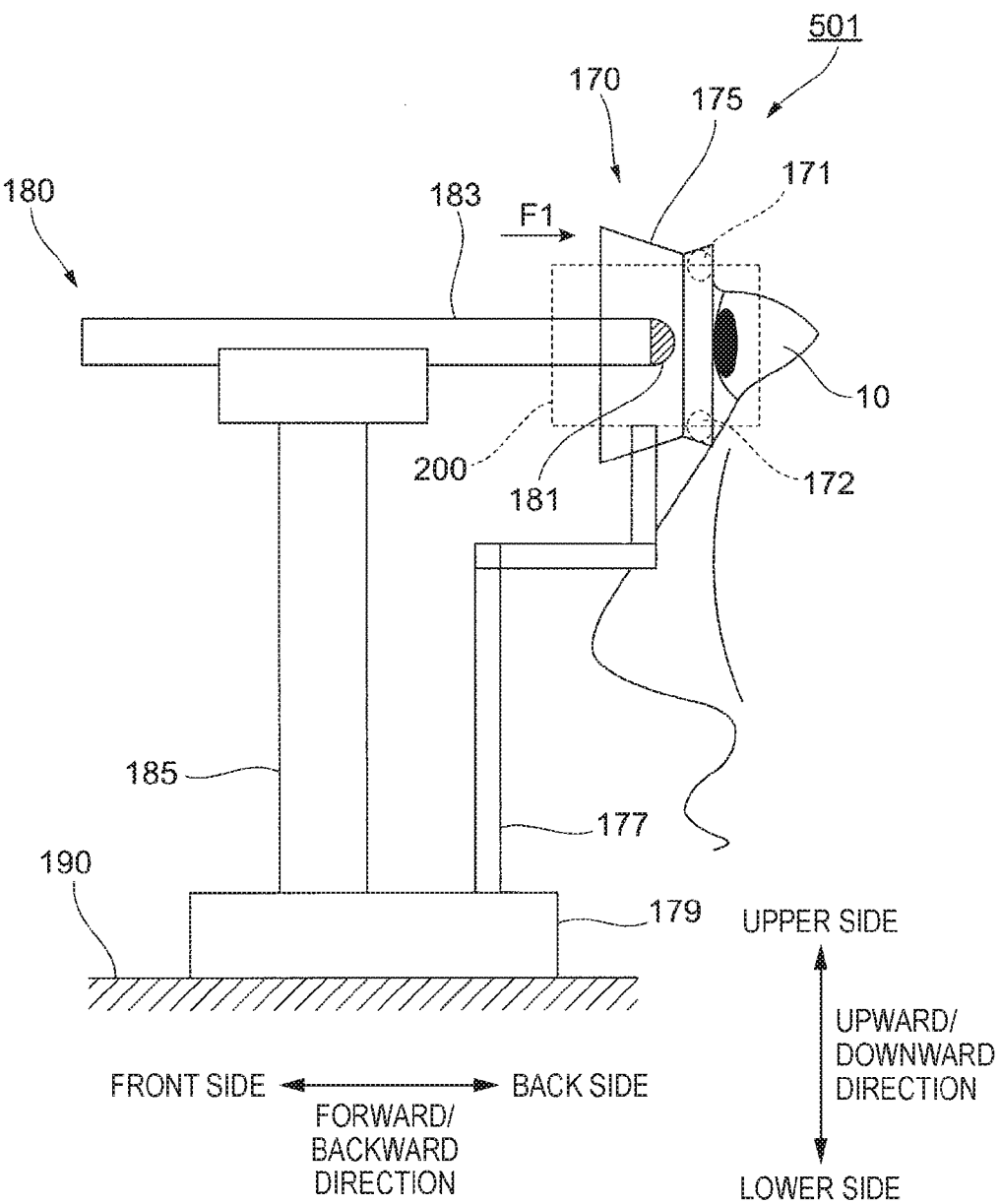
FIG. 9 describes a configuration of an optical measurement apparatus, according to another alternative exemplary embodiment.

FIG. 9 is a view describing a configuration of an optical measurement apparatus 501, according to another alternative exemplary embodiment.

In the above-described optical measurement apparatus 1 illustrated in FIG. 1 and the like, description is given regarding the configuration in which the position of the inner canthus squeezing portion 80 is fixed. However, the configuration is not limited thereto. For example, as in the optical measurement apparatus 501 illustrated in FIG. 9, the inner canthus squeezing portion 80 may be configured to move.

Specifically, the optical measurement apparatus 501 illustrated in FIG. 9 includes an eyelid pressing section 170 that comes into contact with an eyelid of the measurement subject and presses the eyelid, a movable squeezing portion 180 that squeezes the inner canthus side of the eyelid of the measurement subject, and an optical system 200 that is used for measuring the characteristics of the aqueous humor in the eyeball 10 of the measurement subject, similar to the optical measurement apparatus 1 illustrated in FIG. 1 and the like.

The eyelid pressing section 170 includes an upper eyelid pressing section 171, a lower eyelid pressing section 172, a holding member 175 which holds the upper eyelid pressing section 171 and the lower eyelid pressing section 172, a support member 177 which supports the holding member 175, and a base portion 179 which supports the support member 177.

In addition, similar to the optical measurement apparatus 1 illustrated in FIG. 1 and the like, the movable squeezing portion 180 includes an inner canthus squeezing portion 181 which squeezes the skin 24A on the periphery of the inner canthus of the measurement subject, a moving portion 183 which is provided with the inner canthus squeezing portion 181 and moves in the forward/backward direction, and a slide support portion 185 which slidably supports the moving portion 183. The moving portion 183 in this example moves in the forward/backward direction by receiving driving from a motor (not illustrated). In addition, the slide support portion 185 is fixed to the base portion 179.

In addition, the optical system 200 in this example is fixed to the moving portion 183 of the movable squeezing portion 180. The optical system 200 moves in the forward/backward direction together with the moving portion 183.

Subsequently, an operation of the optical measurement apparatus 501 will be described.

First, the optical measurement apparatus 501 is fixedly provided in a work table 190 or the like. The measurement subject presses the face against the optical measurement apparatus 501 at a position where the eyelid of the measurement subject comes into contact with the upper eyelid pressing section 171 and the lower eyelid pressing section 172 of the optical measurement apparatus 501. In this state, for example, when an operation button (not illustrated) is operated, a motor (not illustrated) is driven.

In response to the driving of the motor, the slide support portion 185 moves to the back side in the forward/backward direction (refer to arrow F1). Accordingly, the inner canthus squeezing portion 181 attached to the tip of the slide support portion 185 squeezes the inner canthus side of the eyelid of the measurement subject to the back side in the forward/backward direction. As a result thereof, the optical path 28 (refer to FIG. 1) passing through the aqueous humor is more reliably ensured. In this state, a measurement of the characteristics of the aqueous humor in the eyeball 10 is executed by the optical system 200.

Here, description is given regarding the configuration in which the optical system 200 is fixed to the moving portion 183 of the movable squeezing portion 180. However, the configuration is not limited thereto. For example, a configuration of moving in the forward/backward direction by the driving different from that of the moving portion 183 of the movable squeezing portion 180 may be applied. Otherwise, the position of the optical system 200 may be fixed.

In addition, here, description is given regarding the configuration in which the moving portion 183 moves by receiving driving force from a motor (not illustrated). However, the configuration is not limited thereto. For example, a configuration in which a measurer or the like operating the optical measurement apparatus 501 manually moves the moving portion 183 may be applied.

In addition, here, description is given regarding the configuration in which the movable squeezing portion 180 is provided in the optical measurement apparatus 501 which is fixed onto the work table 190 or the like. However, the configuration is not limited thereto. For example, in the above-described optical measurement apparatus 1 illustrated in FIG. 1 and the like, a configuration provided with the movable squeezing portion 180 may be applied. That is, a configuration in which the inner canthus squeezing portion 80 (FIG. 1) provided in the main body 50A (refer to FIG. 1) moves in the forward/backward direction may be applied.

Modification Example

In the description above, description is given regarding the configuration in which the inner canthus squeezing portion 80 squeezes (pressurizes) the skin 24A on the periphery of the inner canthus. However, the configuration is not limited thereto. For example, a form of squeezing only the skin 24E on the outer canthus side, or a form of squeezing both the skin 24A on the periphery of the inner canthus and the skin 24E on the outer canthus side may be applied. In a case where the skin 24E on the periphery of the outer canthus is squeezed into the eye socket 17, a member similar to the inner canthus squeezing portion 80 may be provided at the tip of the light reception system 23.

In addition, in the description above, description is given regarding the configuration in which the inner canthus squeezing portion 80 is configured with a single member. However, the configuration is not limited thereto. A form in which the inner canthus squeezing portion 80 is configured with plural members may be applied. Specifically, for example, the inner canthus squeezing portion 80 may be configured with two members pressurizing the upper eyelid 18 and the lower eyelid 19 included in the skin 24A on the periphery of the inner canthus.

In addition, the shape of the inner canthus squeezing portion 80 is not particularly limited. Specifically, as long as the inner canthus squeezing portion 80 is in contact with the skin 24A on the periphery of the inner canthus and a state where a gap is formed to the extent that light traveling across the eyeball 10 can pass through may be maintained, a different shape such as a spherical member, an arc-shaped member, and a plate-shaped member may also be applied naturally.

In addition, the position where the inner canthus squeezing portion 80 is provided in the optical measurement apparatus 1 is not particularly limited. Specifically, it is favorable as long as the inner canthus squeezing portion 80 may squeeze the skin 24A on the periphery of the inner canthus to the inward side (back side). A configuration in which the inner canthus squeezing portion 80 is held by the light emission system holding section 50D, or a configuration in which the inner canthus squeezing portion 80 is fixed to the first mirror 29 via a different member may be applied.

In addition, in the description above, description is given regarding the configuration in which the eyelid pressing section 70 includes plural members (upper eyelid pressing section 71 and lower eyelid pressing section 72). However, the configuration is not limited thereto. For example, the eyelid pressing section 70 may be configured with any one of the upper eyelid pressing section 71 and the lower eyelid pressing section 72. Otherwise, a configuration in which the upper eyelid pressing section 71 and the lower eyelid pressing section 72 are integrally formed may be applied.

In addition, the upper eyelid pressing section 71 and the lower eyelid pressing section 72 may have a shape different from that described above. Specifically, as long as the upper eyelid pressing section 71 and the lower eyelid pressing section 72 come into contact with at least any of the upper eyelid 18 and the lower eyelid 19 (refer to FIG. 3B) and a state where a gap is formed to the extent that light can pass through between the upper eyelid 18 and the lower eyelid 19 may be maintained, a different shape such as a hemispherical member, a plate-shaped member, and the like may also be applied naturally.

In addition, any one of the upper eyelid pressing section 71 and the lower eyelid pressing section 72 may be configured to move as described in FIG. 9 and the other one may be configured to be fixed. For example, a configuration in which the upper eyelid pressing section 71 is movable and the lower eyelid pressing section 72 is fixed may be applied.

In addition, description is given regarding the configuration in which the eyelid pressing section 70 (upper eyelid pressing section 71 and lower eyelid pressing section 72) directly presses the eyelids of the measurement subject. However, as long as the eyelid pressing section 70 comes into contact with the skin or the like on the periphery of the eyeball 10 of the measurement subject and the eyelids of the measurement subject are maintained in an open state, the configuration is not limited thereto.

The skin on the periphery of the eyeball 10 denotes a region within a range in which when the inner canthus squeezing portion 80 and the eyelid pressing section 70 come into contact therewith, movement (opening and closing) of at least any one of the upper eyelid 18 and the lower eyelid 19 is restricted.

In addition, description is given regarding the configuration in which the inner canthus squeezing portion 80 and the eyelid pressing section 70 are formed of a silicone resin (silicone). However, the configuration is not limited thereto. For example, the inner canthus squeezing portion 80 and the eyelid pressing section 70 may be configured with a different resin, metal, or the like. In addition, the inner canthus squeezing portion 80 and the eyelid pressing section 70 may be formed by coating a resin body formed of vinyl chloride or the like with an acrylic adhesive. Moreover, for example, a configuration in which pressure sensitive adhesive tapes for medical use are provided on the outer circumferential surfaces of the inner canthus squeezing portion 80 and the eyelid pressing section 70 may be applied.

It is preferable that the inner canthus squeezing portion 80 and the eyelid pressing section 70 are formed of a material having high frictional force and a high level of safety.

In addition, in the description above, description is given regarding the configuration in which the light emission system 21 is disposed on the nose side (inner canthus side) and the light reception system 23 is disposed on the ear side (outer canthus side). However, an opposite configuration, that is, a configuration in which the light emission system 21 is disposed on the nose side and the light reception system 23 is disposed on the ear side may be applied.

In addition, the optical path 28 is not limited to the illustrated configuration. It is favorable that light emitted from the light emission portion 25 is set to pass through so as to travel across the anterior chamber 13 and is set to be received by the light reception portion 35. In addition, the expression "light passes through so as to travel across the anterior chamber 13" denotes that in a case where the eyeball 10 is viewed from the front, light passes through at an angle (that is, within a range less than ±45° with respect to the horizontal axis in the inward/outward direction) closer to the inward/outward direction than the upward/downward direction, including a case where light obliquely passes through in the forward/backward direction.

In addition, in the description above, description is given regarding the configuration in which the light emission system 21 disposed on the nose side protrudes to a side further to the front than the light reception system 23 disposed on the ear side. However, the configuration is not limited thereto. For example, a configuration in which the light emission system 21 and the light reception system 23 are disposed at corresponding positions (the same positions) in the forward/backward direction, or a configuration in which the light reception system 23 disposed on the ear side protrudes to a side further to the front than the light emission system 21 disposed on the nose side may be applied.

In addition, in the description above, description is given regarding the method of calculating the concentration of the intended optically active substance contained in the aqueous humor. However, a configuration in which different characteristics of the aqueous humor are measured may be applied.

In addition, not only the characteristics related to the aqueous humor, a configuration described in the present exemplary embodiment in order to obtain the characteristics related to the cornea or the like which is present in the optical path 28 may be applied. That is, as long as the apparatus allows light to be incident from the outside of the eyeball 10, allows the light to pass through the aqueous humor in the cornea 14 and the anterior chamber 13, and receives the light which has passed through thereof, the configuration described in the present exemplary embodiment may be applied.

In addition, in description of the present exemplary embodiment, description is given regarding a case of the eyeball 10 of the left eye. However, naturally, the optical measurement apparatus 1 may be applied to the eyeball of the right eye (not illustrated).

In addition, various types of exemplary embodiments and the modification example are described above. However, naturally, a configuration in which the exemplary embodiments and the modification example are combined together may also be applied.

In addition, the present disclosure is not limited by the exemplary embodiments at all and may be executed in various types of forms without departing from the scope and the gist of the present disclosure.

What is claimed is:

1. An optical measurement apparatus comprising:
an emission section that emits light such that the light travels across an anterior chamber of an eyeball of a measurement subject;
a light reception section that receives light which is emitted from the emission section and travels across the anterior chamber; and
a positioning section that performs positioning of one of the emission section and the light reception section at a position where skin on a periphery of an inner canthus of the eyeball is squeezed into an eye socket accommodating the eyeball.

2. The optical measurement apparatus according to claim 1, wherein
the positioning section performs positioning of the one of the emission section and the light reception section at a position different from a position of the inner canthus in an upward/downward direction of the eyeball, on the skin on the periphery of the inner canthus.

3. The optical measurement apparatus according to claim 1, wherein
the positioning section performs positioning of the one of the emission section and the light reception section at a position substantially same as a position of the inner canthus in the upward/downward direction of the eyeball, on the skin on the periphery of the inner canthus.

4. The optical measurement apparatus according to claim 1, wherein
the one of the emission section and the light reception section includes a squeezing portion that squeezes the skin on the periphery of the inner canthus into the eye socket.

5. The optical measurement apparatus according to claim 4, wherein
the squeezing portion is softer than a holding portion that holds the squeezing portion in the one of the emission section and the light reception section.

6. The optical measurement apparatus according to claim 4, wherein
a part of the squeezing portion coming into contact with the skin on the periphery of the inner canthus is formed of a curved surface.

7. The optical measurement apparatus according to claim 4, wherein
the one of the emission section and the light reception section protrudes toward an inward side with respect to the eye socket beyond other of the emission section and the light reception section.

8. A light irradiation/reception method comprising:
causing an emission section to emit light such that the light travels across an anterior chamber of an eyeball of a measurement subject;
causing a light reception section to receive light which travels across the anterior chamber; and
positioning of one of the emission section and the light reception section at a position where skin on a periphery of the eyeball is squeezed into an eye socket accommodating the eyeball.

9. An optical measurement apparatus comprising:
an emission section that emits light such that the light travels across an anterior chamber of an eyeball of a measurement subject:
a light reception section that receives light which is emitted from the emission section and travels across the anterior chamber;
a positioning section that performs positioning of one of the emission section and the light reception section at a position where skin on a periphery of an inner canthus or on a periphery of an outer canthus of the eyeball is squeezed into an eye socket accommodating the eyeball; and
a restraint section that restrains an exposed region of the eyeball from being narrow due to the positioning.

10. The optical measurement apparatus according to claim 9, wherein
the one of the emission section and the light reception section includes a squeezing portion that squeezes the skin on the periphery of the inner canthus or on the periphery of the outer canthus into the eye socket.

11. The optical measurement apparatus according to claim 9, wherein
the restraint section includes an upper eyelid pressing portion that presses an upper eyelid of the measurement subject and a lower eyelid pressing portion that presses a lower eyelid of the measurement subject.

12. The optical measurement apparatus according to claim 11, wherein the upper eyelid pressing portion and the lower eyelid pressing portion respectively move away from each other.

13. A light irradiation/reception method comprising:

causing an emission section to emit light such that the light travels across an anterior chamber of an eyeball of a measurement subject;

causing a light reception section to receive light which travels across the anterior chamber;

positioning of one of the emission section and the light reception section at a position where skin on a periphery of the eyeball or on a periphery of an outer canthus is squeezed into an eye socket accommodating the eyeball; and restraining an exposed region of the eyeball from being narrow due to the positioning.

* * * * *